(12) United States Patent
Oda et al.

(10) Patent No.: US 6,605,705 B1
(45) Date of Patent: Aug. 12, 2003

(54) PROSTAGLANDIN D SYNTHASE-SPECIFIC MONOCLONAL ANTIBODY

(75) Inventors: Hiroshi Oda, Ibaraki (JP); Nobuyuki Sato, Ibaraki (JP); Masazumi Nishikawa, Ibaraki (JP); Kosuke Seiki, Ibaraki (JP); Yoshihiro Urade, Kyoto (JP); Fumitaka Saji, Hyogo (JP)

(73) Assignees: Maruha Corporation, Tokyo (JP); Osaka Bioscience Institute, Osaka (JP)

( * ) Notice: Subject to any disclaimer, the term of this patent is extended or adjusted under 35 U.S.C. 154(b) by 0 days.

(21) Appl. No.: 09/066,357

(22) PCT Filed: Oct. 31, 1996

(86) PCT No.: PCT/JP96/03190

§ 371 (c)(1),
(2), (4) Date: Apr. 28, 1998

(87) PCT Pub. No.: WO97/16461

PCT Pub. Date: May 9, 1997

(30) Foreign Application Priority Data

Oct. 31, 1995 (JP) ............................................. 7-283859
Mar. 14, 1996 (JP) ............................................. 8-057841
Jun. 10, 1996 (JP) ............................................. 8-147689
Aug. 22, 1996 (JP) ............................................. 8-221530

(51) Int. Cl.[7] .................. C12P 21/08; C12P 21/04; C07K 16/00; C12N 5/06; G01N 33/53

(52) U.S. Cl. .................. 530/388.26; 530/388.1; 530/387.1; 530/809; 435/70.21; 435/326; 435/346; 435/975; 436/548

(58) Field of Search ......................... 530/388.1, 388.26, 530/387.1, 805, 809; 935/89; 435/7.1, 70.21, 183, 975, 326, 346, 7.4, 705, 709, 240.26; 436/808, 548; 424/130.1, 146.1

(56) References Cited

U.S. PATENT DOCUMENTS 4,758,655 A * 7/1988 Houghten .................. 530/324
6,019,973 A * 2/2000 Hilmgren et al. ........ 424/185.1

OTHER PUBLICATIONS

Zahn et al. Neuroscience Letters 154: 93–95, 1993.*
Shimizu et al., *J. Biol. Chem.* (1979) 254/11:5222–5228.
Urade et al., *J. Biol. Chem.* (1985) 260/22:12410–12415.
Urade et al., *J. Biol. Chem.* (1990) 265/1:371–375.
Urade et al., *J. Biol. Chem.* (1987) 262/8:3820–3825.
Urade et al. J. Biol. Chem. 262: 15132–15136, 1987.*
Masayoshi et al. Proc. Natl. Acad. Sci. 84: 7677–7680, 1987.*
Nagata et al. Proc. Natl. Acad. Sci. 88: 4020–4024, 1991.*
Melegos et al. Clin Chem. 42: 1984–1991, 1996.*
Olsson, In: XXIVth Colloquium: Peptides of Biological Fluids, Ed. H. Peeters, Pergmon Press, 24: 147–150, 1976.*
Hiraoka et al. Biol. Pharm. Bulletin 16: 949–952, abstract, 1993.*
Diamandis et al. Clin. Chem. 37: 625–636, 1991.*
Watanabe et al. Biochem. Biophys. Res. Commun. 203: 1110–1116, 1994.*
Killian et al. Biol. Reprod. 49: 1202–1207, abstract, 1993.*
Brock et al. Clin. Genetics 9: 385–388, 1976.*
Olsson et al. J. Reproduct. Fertility 42: 149–151, 1975.*
Olsson et al. J. Neurol. Neurosurg. Pasychiatr. 37: 302–311, 1974.*
Olsson et al. J. Neurochem. 21: 625–633, 1973.*
Hoffmann et al. J. Neurochem. 61: 451–456, 1993.*
Harrington et al. Appl. Theor. Electrophor. 3: 229–234, abstract, 1993.*
Felgenhauer et al. Klin. Wochenschr. 65: 764–768, abstract, 1987.*
Köhler et al. (1975) "Continuous cultures of fused cells secreting antibody of predefined specificity", Nature 256:495–497.
Grabenhorst et al. (1995) "Construction of stable BHK–21 cells coexpressing human . . . protein" Eur. J. Biochem. 232:718–725.
Kuruvilla et al. (1991) "Isolation and amino terminal sequence of β–trace, a novel protein from human cerebrospinal fluid" Brain Research 565:337–340.
Olsson et al. (1976) "Immunoglobulin abnormalities in multiple sclerosis" J. of Neurological Sciences 27:233–245.

* cited by examiner

Primary Examiner—S. Devi
(74) Attorney, Agent, or Firm—Fish & Richardson P.C.

(57) ABSTRACT

The invention relates to a monoclonal antibody specifically recognizing lipocalin-type prostaglandin D synthase (L-PGDS), a hybridoma producing the monoclonal antibody, methods for detection of L-PGDS or diseases by the monoclonal antibody, and a kit for detection of L-PGDS by the monoclonal antibody. According to the invention, there is provided a monoclonal antibody specific to L-PGDS.

11 Claims, 12 Drawing Sheets

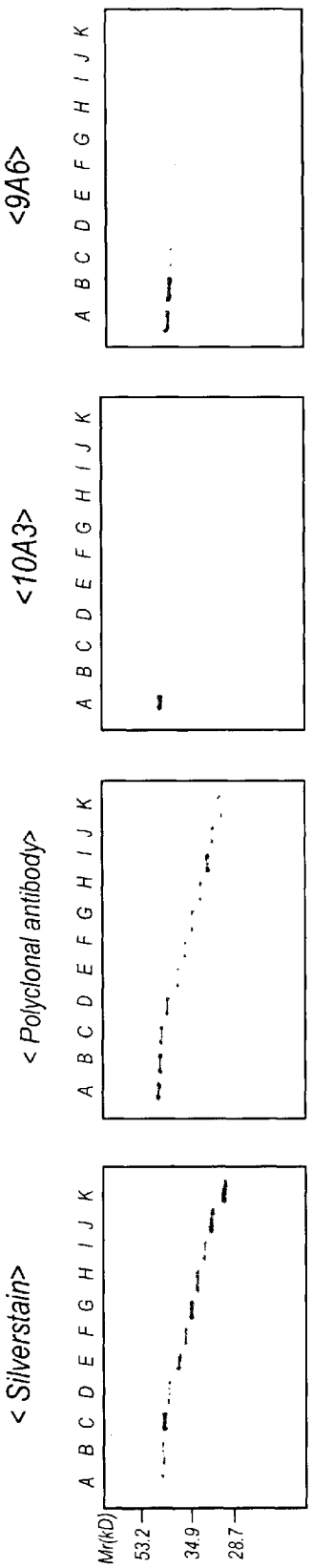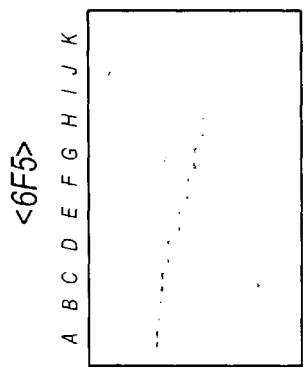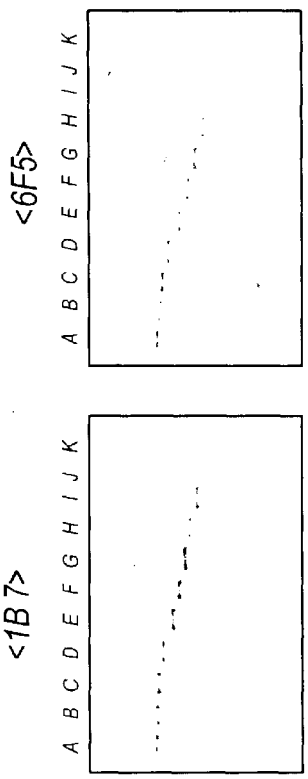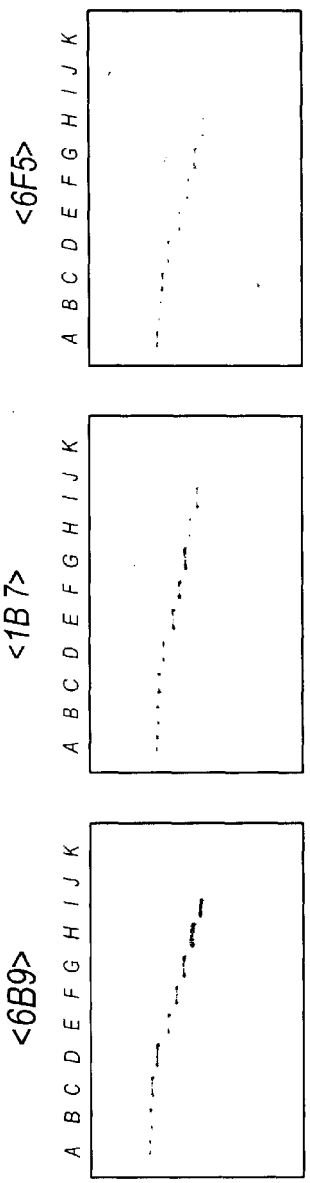
FIG. 4A  <Silverstain>
FIG. 4B  <Polyclonal antibody>
FIG. 4C  <10A3>
FIG. 4D  <9A6>
FIG. 4E  <6B9>
FIG. 4F  <1B7>
FIG. 4G  <6F5>

LANE 1: CSF (NOT PURIFIED)
LANE 2: FRACTION NOT ADSORBED ON THE GEL (PASSING FRACTION)
LANE 3: FRACTION ELUTED WITH 0.1 M SODIUM CITRATE (pH 3.0)

PROSTAGLANDIN D SYNTHASE-SPECIFIC MONOCLONAL ANTIBODY

FIELD OF THE INVENTION

The present invention relates to a monoclonal antibody specific to human L-PGDS present predominantly in cerebrospinal fluid (CSF), a hybridoma producing said monoclonal antibody, methods for detection of L-PGDS or diseases by said monoclonal antibody, and a kit for detection of L-PGDS by said monoclonal antibody.

BACKGROUND OF THE INVENTION

Prostaglandin D is a biologically active substance synthesized in animal tissues from arachidonic acid released from a biomembrane upon stimulation, and it is produced from prostaglandin H (a common precursor of prostaglandin families produced by cyclo-oxygenase) by prostaglandin D synthase (PGDS).

The presence of two types of PGDS, glutathione-independent L-PGDS and glutathione-dependent spleen type PGDS, is known (Shimizu et, al., J. Biol. Chem., 254, 5222–5228 (1979); Urade et al., J. Biol. Chem., 260, 12410–12415 (1985); Christ-Hazelhof and Nugteren, Biochim. Biophys. Acta, 572, 43–51 (1979); Urade et al., J. Biol. Chem., 262, 3820–3825 (1987). The former is known to be predominantly located in the central nervous system such as brain, epididymis, spinal cord, retina, and inner ear (Urade et al., J. Biol. Chem., 260, 12410–12415 (1985); Ueno et al., J. Neurochem., 45, 483–489 (1985); Urade et al., J. Biol. Chem., 262, 3820–3825 (1987); Goh et al., Biochim. Biophys. Acta, 921, 302–311 (1987); and Tachibana et al., Proc. Natl. Acad. Sci. USA, 84, 7677–7680 (1987)), and the latter is known to be distributed broadly in almost all peripheral organs including spleen, bone marrow, digestive organs, thymus, and skin (Ujihara et al., Arch. Biochem. Biophys., 260, 521–531 (1988); and Ujihara et al., J. Invest., Dermatol., 90, 448–451 (1988)).

On the other hand, a protein called β-trace was observed to be present specifically in human CSF, but its physiological function remained unrevealed (Causen, J. Proc. Soc. Exp. Biol. Med., 107, 170–172 (1961)).

A certain correlation between β-trace known as a protein specific to CSF and severe brain disorders or certain diseases (multiple sclerosis, brain tumors, Meckel's syndrome and paraproteinemia) was noted from the observation that β-trace levels depend on such disorders (Ericsson et al., Neurology, 19, 606–610 (1969); Olsson et al., J. Neurol. Neurosurg. Psychiat. 37, 302–311 (1974); Link, J. Neurol. Sci., 16, 103–114 (1972); Whistsed and Penny, Clinica Chimica Acta, 50, 111–118 (1974); and Chemke et al., Clinical Genetics, 11, 285–289 (1977)). However, the exact correlation between β-trace and such disorders could not be determined because the physiological function of β-trace still remained unrevealed and because there was no tool available for determining the exact amount (concentration) of β-trace.

Recently, the nucleotide sequence of cDNA coding for L-PGDS was reported (Nagata et al., Proc. Natl. Acad. Sci. USA, 88, 4020–4024 (1991)), and production of L-PGDS by genetic recombination became feasible. The L-PGDS thus produced was examined and its amino acid sequence was estimated and compared with an N-terminal partial amino acid sequence of human β-trace in searching for their homology (Kuruvilla et al., Brain Research, 565, 337–340 (1991), Zahn et al., Neuroscience Letters, 154, 93–95 (1993)) or with the amino acid sequence of purified human β-trace (Hoffmann et al., J. Neurochem., 61(2), 451–456 (1993)), and further immunological examination was made using polyclonal antibodies (Watanabe et al., Biochem. Biophys. Res. Communication, 203, 1110–1116 (1994)). These studies revealed that β-trace was identical with L-PGDS.

Prostaglandin D occurring abundantly in the central nervous system functions, in one physiological action, as a neuromodulator of several central actions including sleep promotion. Prostaglandin D synthase is considered as a key enzyme for sleep-wake activities (Hayashi, FASEB J., 5, 2575–2581 (1991)), and it is believed that at least a part of the L-PGDS secreted from competent cells is accumulated in CSF (Watanabe et al., Biochem. Biophys. Res. Communication, 203, 1110–1116 (1994)).

Accordingly, the analysis of L-PGDS distribution etc. in the central nervous system is useful for detection of diseases in the central nervous system, and it is expected that L-PGDS levels in CSF or humor can also be used as an indicator in early diagnosis and prognostic observations for other diseases caused by abnormalities in the central nervous system. It is further expected that L-PGDS (or β-trace) can be used for examination of a reproduction ability, diagnosis of fetal growth, etc. because this enzyme is distributed in such humors derived from genital organs, as semen, oviduct fluid and amniotic fluid, as well. For such applications, there is demand for antibodies specifically recognizing L-PGDS.

Nevertheless, such antibodies have still not been established with high specificity to meet such demand.

DISCLOSURE OF THE INVENTION

The object of the present invention is to provide a monoclonal antibody specifically recognizing L-PGDS, a hybridoma producing said antibody, methods for detection of L-PGDS or diseases by said monoclonal antibody, and a kit for detection of L-PGDS by said monoclonal antibody.

As a result of their eager researches, the present inventors have successfully obtained a monoclonal antibody specifically recognizing L-PGDS from a hybridoma prepared by cell fusion between myeloma cells and antibody-producing cells from an animal immunized with L-PGDS which is a major protein in human CSF, and they thereby arrived at the present invention.

That is, the present invention relates to a monoclonal antibody specifically recognizing L-PGDS. The subclass of such monoclonal antibody includes immunoglobulin G1 or G2.

Further, the present invention relates to a hybridoma producing said monoclonal antibody by cell fusion between myeloma cells and antibody-producing cells from an animal immunized with L-PGDS.

Further, the present invention relates to methods for detection of L-PGDS or diseases by said monoclonal antibody. An example of such diseases is oligospermia.

Further, the present invention relates to a kit for detection of L-PGDS, which is selected from a reagent containing said monoclonal antibody labeled with an enzyme and a substrate solution, and a reagent containing said monoclonal antibody obtained by biotination, enzyme-labeled avidin, and a substrate.

Further, the present invention relates to a method for detection of diseases by said kit for detection of L-PGDS. An example of such diseases is oligospermia.

Hereinafter, the present invention is described in detail.

1. Production of the Monoclonal Antibody

Production of the present monoclonal antibody against L-PGDS consists of the steps of:
(1) Preparation of an antigen;
(2) Immunization and preparation of antibody-producing cells;
(3) Establishment of an antibody-titration system;
(4) Cell fusion;
(5) Selecting and cloning hybridomas; and
(6) Isolation of the monoclonal antibody.

Hereinafter, each step is described.

(1) Preparation of an Antigen

L-PGDS can be produced in large amounts in a usual manner by *E. coli* and CHO cells etc. with its known cDNA (Nagata et al., Proc. Natl. Acad. Sci. USA, 88, 4020–4024 (1991)). In this production of L-PGDS, a recombinant DNA containing the cDNA for L-PGDS is constructed and transformed into a microorganism, which is then cultured to produce the enzyme. The L-PGDS thus produced can be purified from the culture by conventional means.

Then, an immunogen is prepared by dissolving the resulting L-PGDS in a buffer and then adding an adjuvant to it. Examples of such adjuvants are Freund complete adjuvant, Freund incomplete adjuvant, BCG, Hunter's Titermax (CytRx Corporation), key hole limpet hemocyanin-containing oil, etc., and any of them can be mixed.

(2) Immunization and Preparation of Antibody-producing Cells

The immunogen thus obtained is administered as antigen into mammals such as horse, monkey, dog, pig, cow, goat, sheep, rabbit, guinea pig, hamster and mouse, or birds such as pigeon and chicken. In particular, mouse, rat, guinea pig, rabbit and goat are preferably used. Any of the known immunization methods may be employed preferably using i.v., s.c., or i.p. administration. Immunization intervals are not particularly limited, and the immunogen is given 2 to 10 times, preferably 2 to 5 times, preferably at intervals of several days to several weeks, more preferably 1 to 3 weeks.

1 to 10 days preferably 2 to 5 days after the final immunization, antibody-producing cells are prepared from the animal. Examples of such antibody-producing cells are spleen cells, lymph node cells, thymocytes and peripheral blood cells, and generally spleen cells are used conventionally. In the case of mouse, 0.01 µg to 1,000 µg, preferably 1 to 300 µg antigen is given per animal in one administration.

(3) Establishment of an Antibody-titration System

It is necessary to establish a system of measuring the antibody titer in serum from the immunized animal or in a culture supernatant from the antibody-producing cells, so that the immune response level of the immunized animal can be confirmed and the desired hybridoma can be selected from the fusion cells. For example, the antibody can be detected conventionally using known methods such as enzyme immunoassay (EIA), radioimmunoassay (RIA), enzyme-linked immunosorbent assay (ELISA) and fluorescence immunoassay (FIA). Although the present method for detecting the antibody is not limited to the above methods, ELISA is conveniently used for easy operations. Usually, L-PGDS is put to each well of a 96-well plastic microtiter plate and left at room temperature to immobilize the enzyme onto the well. Then, the unbound sites of the L-PGDS as antigen are blocked with calf serum albumin, fetal bovine serum, skim milk, or gelatin. Then, an antiserum diluted with phosphate buffered saline (referred to hereinafter as PBS) or a culture supernatant of the hybridoma is added to each well. Subsequently, commercial secondary antibody labeled with an enzyme or fluorescent compound or with biotin is added to each well, followed by adding a coloration substrate. The coloration occurring can be determined in a photometer or fluorometer to quantify the antibody against L-PGDS.

(4) Cell Fusion

The myeloma cells to be subjected to cell fusion with the antibody-producing cells are those derived from animal species such as mouse, rat, and human, easily available to those skilled in the art. The cell line used is preferably drug-resistant, which upon fusion with the antibody-producing cells, is rendered survivable in a selection medium such as HAT medium. A cell line resistant to 8-azaguanine is generally used. Because such cell line lacks hypoxanthine-guanine phosphoribosyltransferase (HGPRT-), it can not grow in hypoxanthine-aminopterine-thymidine (HAT) medium. The cell line used is preferably cells not secreting immunoglobulins.

Examples of such myeloma cells are mouse myeloma cell lines such as P3X63Ag8 (ATCC TIB-9; Nature, 256, 495–497 (1978)), P3X63Ag8U.1 (P3U1) (ATCC CRL-1580; Current Topics in Microbiology and Immunology, 81, 1–7 (1978), P3X63Ag8.653 (ATCC TIB-18; European J. Immunology, 6, 511–519 (1976)), and P2/NSI/1-Ag4-1 (ATCC CRL-1581; Nature, 276, 269–270 (1978)); rat myeloma cell lines such as for example 210.RCY.Ag1.2.3 (Y3-Ag1.2.3) (ATCC CRL-1631; Nature, 277, 131–133 (1979)); human myeloma cell lines such as U-266-AR1 (Proc. Natl. Acad. Sci. USA, 77, 5429 (1980)), GM 1500 (Nature, 288, 488 (1980)), and KR-4 (Proc. Natl. Acad. Sci. USA, 79, 6651 (1982)).

The antibody-producing cells are obtained from spleen cells, lymph node cells, thymocytes, and peripheral blood cells. Briefly, the antibody-producing cells are prepared as follows: Tissues such as spleen, lymph node or thymus are excised or blood are collected from the immunized animals. These tissues are disrupted and then suspended in a buffer such as PBS or in a medium such as DMEM, RPMI 1640 and E-RDF. This cell suspension is filtered through e.g. a #200–250 stainless mesh and then centrifuged to give the desired antibody-producing cells.

Then, the antibody-producing cells are subjected to cell fusion with myeloma cells.

Before cell fusion, myeloma cells suitable for antibody production are selected. $10^6$ to $10^8$ cells/ml antibody-producing cells are mixed with $10^6$ to $10^8$ cells/ml myeloma cells at a ratio of from 1:1 to 1:10 in an animal cell growth medium, e.g. Eagle's minimal essential medium (MEM), Dulbecco's modified Eagle's medium (DMEM), RPMI-1640 medium, or E-RDF medium. To enhance cell fusion, these cells are mixed at a ratio of e.g. 1:6 and then incubated for 1 to 15 minutes in the presence of a fusion enhancer in e.g. RPMI-1640 medium containing dimethylsulfoxide at a temperature of 30 to 37° C. This fusion enhancer may be polyethylene glycol with an average molecular weight of 1,000 to 6,000, polyvinyl alcohol or Sendai virus. Alternatively, the antibody-producing cells can be subjected to cell fusion with myeloma cells by electric stimulation (e.g. electroporation) in a commercial cell fusion apparatus.

(5) Selection and Cloning of Hybridomas

After cell fusion, the cells are screened for desired hybridomas. The selective growth of the fusion cells in a selection medium may be used for screening as follows: The cell suspension is diluted 5- to 10-fold with e.g. E-RDF medium containing 15% fetal bovine serum and then put to each well of a microtiter plate at about $10^2$ to $10^6$ cells/well, followed by addition of a selection medium (e.g. HAT medium) to each well. Thereafter, the cells are incubated while the selection medium is exchanged with fresh one at suitable intervals.

Where myeloma cells are from an 8-azaguanine-resistant strain and HAT medium is used as selection medium, the myeloma cells and antibody-producing cells, if they fail to fuse, will die during in vitro culture in about 7 days and antibody-producing cells in 10 days. Hence, hybridomas can be obtained from those cells beginning to grow after the 10th day of culture.

The hybridomas are screened for the desired ones by examining their supernatants on the presence of the antibodies against L-PGDS. This screening step can be carried out by any of the conventional methods. For example, a supernatant (first antibody) from hybridomas grown in each well is put to a well with L-PGDS immobilized on it, then a labeled secondary antibody is added to the well and incubated, and the binding ability of the secondary antibody is then examined in enzyme immunoassays (EIA, ELISA), RIA, etc.

In more detail, the screening of hybridomas is carried out as follows: Natural or recombinant L-PGDS, which was used as immunogen, is immobilized as antigen onto a 96-well microtiter plate. A culture supernatant expected to contain the monoclonal antibody is added to each well and reacted with the immobilized antigen. Then, the antigen-bound monoclonal antibody, if any, is reacted with another antibody (enzyme-labeled anti-immunoglobulin antibody). Alternatively, said immobilized monoclonal antibody is reacted with a biotinylated anti-immunoglobulin antibody and then with enzyme-labeled avidin. Finally, each well is colored by adding an enzyme substrate solution. The hybridomas whose culture supernatants are colored in the wells having the immobilized natural or recombinant L-PGDS are those producing antibodies having the ability to bind to the L-PGDS.

These hybridomas can be cloned in conventional methods including limiting dilution, soft agar cloning, fibrin gel cloning and fluorescence excitation cell sorting to give the desired monoclonal antibody-producing hybridoma.

(6) Isolation of the Monoclonal Antibody

From the resulting hybridoma, the monoclonal antibody can be isolated using conventional methods such as cell culture method, ascites transudate method, etc.

In the cell culture method, the hybridoma is cultured for 2 to 14 days in a medium such as RPMI-1640, MEM, or E-RDF containing 10 to 20% calf serum or in a serum-free medium under conventional culture conditions, e.g. 37° C., 5% $CO_2$. The antibody can be obtained from the culture.

In the ascites transudate method, a mineral oil such as pristane (2,6,10,14-tetramethylpentadecane) is administrated by i.p. to the same mammal species as the mammal from which the myeloma cells were derived. Then, the hybridoma, $1 \times 10^7$ to $1 \times 10^9$ cells, preferably $5 \times 10^7$ to $1 \times 10^8$ cells, are administrated by i.p. to the animal, and a large amount of hybridoma cells are grown in the animal. After 1 to 4 weeks, preferably 2 to 3 weeks, ascites fluid or serum is collected from the animal.

If it is necessary to purify the antibody from the ascites fluid or serum, it can be purified by conventional methods such as salting-out with ammonium sulfate, ion-exchange chromatography on anion exchanger e.g. DEAE cellulose, affinity chromatography on Protein A SEPHAROSE, and gel filtration, and these may be used singly or in combination.

2. Method of Detecting L-PGDS by the Monoclonal Antibody of the Present Invention The method of detecting L-PGDS according to the present invention can be carried out using said monoclonal antibody, as follows:

A 96-well microtiter plate is coated with a diluted sample such as CSF, serum etc. and then blocked with e.g. 0.2% gelatin in PBS. Then, the monoclonal antibody of the present invention, labeled with an enzyme, is added to each well and then incubated; alternatively, the monoclonal antibody labeled with biotin is added to each well, then the plate is washed, enzyme-labeled avidin or streptoavidin is added to each well, and the plate is further incubated. Then, the plate is washed and a coloration substrate such as ABTS (2,2'-azino-di-(3-ethyl-benzothiazoline-6-sulfonic acid)) is added to each well. L-PGDS can be determined by examining this coloration in the calorimetric method.

In another embodiment of the present invention, a 96-well microtiter plate is coated with the diluted monoclonal antibody of the present invention and then blocked with e.g. 0.2% gelatin in PBS. Then, a diluted sample such as CSF, serum etc. is added to each well and the plate is incubated. After washing the plate, another enzyme-labeled monoclonal or polyclonal antibody solution is added to each well and the plate is incubated; alternatively, the monoclonal antibody or polyclonal antibody labeled with biotin is added to each well, then the plate is washed, enzyme-labeled avidin or streptoavidin is added to each well, and the plate is further incubated. Then, the plate is washed and a coloration substrate such as ABTS (2,2'-azino-di-(3-ethyl-benzothiazoline-6-sulfonic acid)) is added to each well. The L-PGDS can be determined by examining this coloration in the calorimetric method. In this manner, it is possible to detect and quantify L-PGDS.

3. A Reagent for Measurement of L-PGDS by the Monoclonal Antibody of the Present Invention The monoclonal antibody of the present invention is useful as a reagent for measurement of L-PGDS because it specifically binds to L-PGDS. Furthermore, the present monoclonal antibody is useful as a reagent in determining the presence and distribution of not only L-PGDS as antigen but also other similar antigens having the same epitope as that of L-PGDS, as well as fragments of L-PGDS in biological samples such as organs, tissues, cells and humor. Hence, the antibody of the present invention is useful as a reagent for such measurement and diagnosis. The detection or measurement of L-PGDS in organs, tissues, cells and humor can be effected using quantitative or qualitative means such as EIA, ELISA, RIA, FIA, Western blot technique and immunohistochemistry, etc.

4. A Kit for Detection of L-PGDS

The kit of the present invention, if an enzyme is used as a label for detection, contains the following ingredients:
(1) monoclonal antibody labeled with an enzyme; and
(2) substrate.

The kit of the present invention, if modified with the sandwich ELISA method, contains the following ingredients:
(1) monoclonal antibody;
(2) monoclonal or polyclonal antibody labeled with an enzyme; and
(3) substrate.

The kit of the present invention, if modified with the biotin-avidin method, contains the following ingredients:
(1) biotinated monoclonal antibody;
(2) enzyme-labeled avidin or streptavidin; and
(3) substrate.

The kit of the present invention, if modified with the sandwich ELISA and biotin-avidin methods, contains the following ingredients:

(1) monoclonal antibody;
(2) biotinated monoclonal or polyclonal antibody;
(3) enzyme-labeled avidin or streptavidin; and
(4) substrate.

In the ingredients, the "monoclonal antibody" means the monoclonal antibody of the present invention. The "polyclonal antibody" means an antibody contained in serum from an animal immunized with L-PGDS, and it can be prepared in the following manner.

(1) Preparation of the Antigen

L-PGDS can be produced in large amounts in a usual manner by *E. coli* and CHO cells etc. with its known cDNA (Nagata et al., Proc. Natl. Acad. Sci. USA, 88, 4020–4024 (1991)). For production of L-PGDS, a recombinant DNA containing the cDNA for L-PGDS is constructed and transformed into a microorganism, and the transformant is cultured to produce the enzyme. The resulting L-PGDS can be purified from the culture by conventional means.

L-PGDS thus obtained is dissolved in a buffer, and an immunogen is prepared by adding an adjuvant to it. Examples of adjuvants are Freund complete adjuvant, Freund incomplete adjuvant, BCG, Hunter's Titermax (CytRx Corporation), key hole limpet hemocyanin-containing oil, etc., and any of them can be mixed.

(2) Immunization and Preparation of Blood

The immunogen thus obtained is administrated into mammals such as horse, monkey, dog, pig, cow, goat, sheep, rabbit, guinea pig, hamster and mouse, or birds such as pigeon and chicken, among which mouse, rat, guinea pig, rabbit and goat are preferably used. Any of the known immunization methods can be employed preferably via i.v., s.c., or i.p. administration. Immunization intervals are not particularly limited, and this administration is carried out 2 to 10 times, preferably 2 to 5 times, at intervals of preferably several days to several weeks, more preferably 1 to 3 weeks.

Antibody titer in blood from the immunized animal is determined according to the above method in (3) "1. Production of the monoclonal antibody". Blood samples found to have high antibody titer are left at room temperature or 4° C. and centrifuged to give serum containing the polyclonal antibody.

If it is necessary to purify the polyclonal antibody from the serum, it can be purified by conventional methods such as salting-out with ammonium sulfate, ion-exchange chromatography on anion exchanger e.g. DEAE cellulose, affinity chromatography on Protein A Sepharose, and gel filtration separating molecules depending on molecular weight and structure, and these may be used in singly or in combination.

According to the present invention, various diseases can be detected by use of the present kit for detection of L-PGDS. For example, oligospermia can be diagnosed readily and rapidly by the present kit using the monoclonal antibody.

The monoclonal antibody of the present invention can also be used to purify L-PGDS. That is, the monoclonal antibody of the present invention is coupled in a usual manner to carriers such as agarose, cellulose, acrylamide gel, commercially available self-made affinity carriers and then washed. L-PGDS can be purified easily with high yield by elution from the column with a suitable solvent or buffer.

BRIEF DESCRIPTION OF THE DRAWINGS

FIG. 4A shows the result of an epitope mapping of each monoclonal antibody from Silverstrain.

FIG. 4B shows the result of an epitope mapping of each Polyclonal antibody.

FIG. 4C shows the result of an epitope mapping of the monoclonal antibody designated as 10A3.

FIG. 4D shows the result of an epitope mapping of the monoclonal antibody designated as 9A6.

FIG. 4E shows the result of an epitope mapping of the monoclonal antibody designated as 6B9.

FIG. 4F shows the result of an epitope mapping of the monoclonal antibody designated as 1B7.

FIG. 4G shows the result of an epitope mapping of the monoclonal antibody designated as 6F5.

BEST MODE FOR CARRYING OUT THE INVENTION

Figure 1:
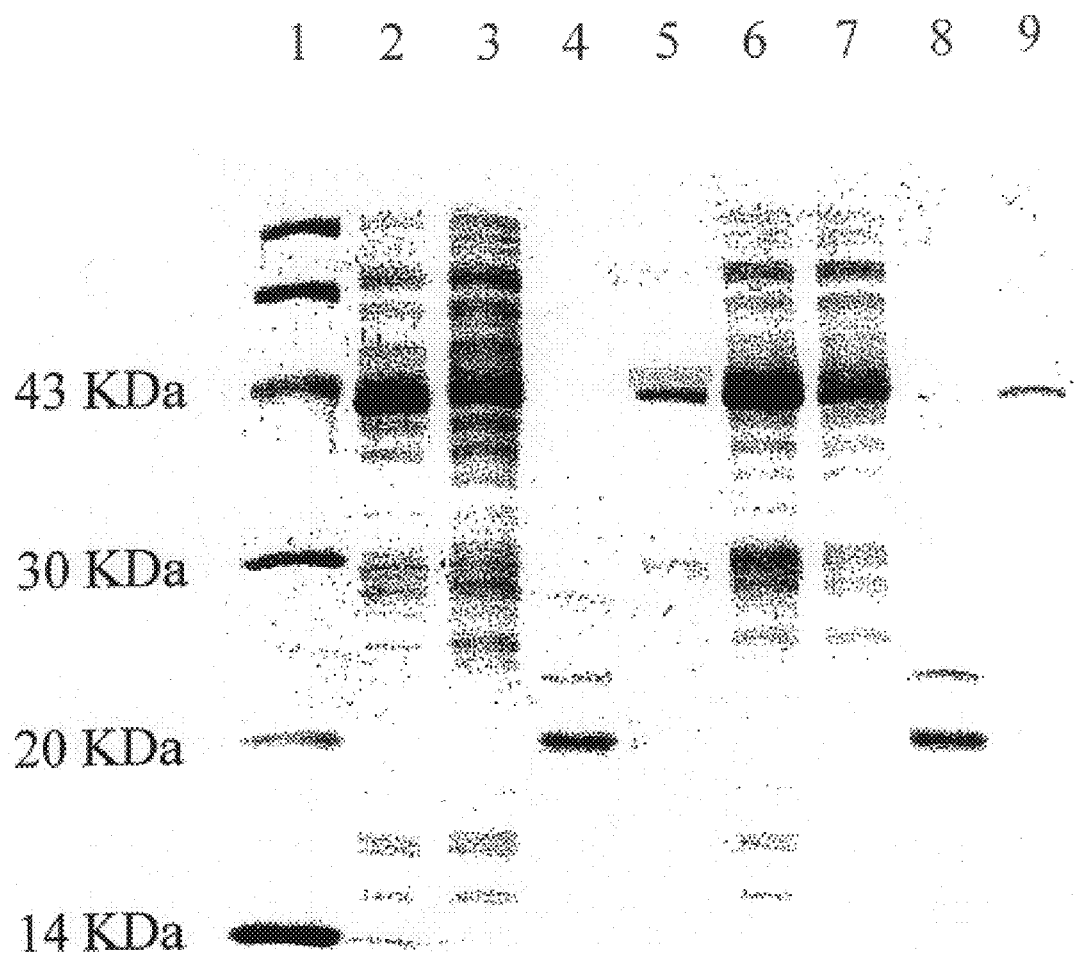
FIG. 1 is a photograph showing a profile in SDS-PAGE.

Hereinafter, the present invention is described in more detail by reference to Examples. However, the present invention is not limited to the Examples.

EXAMPLE 1

Production of the Monoclonal Antibody (1) Preparation of the Antigen

L-PGDS was prepared as antigen by genetic engineering. A GST gene fusion system (Pharmacia) was used for expression of the antigen in *E. coli* and purification. The following procedure was carried out for fusion of L-PGDS with GST protein.

A 185 bp product was obtained by amplifying a region of cDNA coding for N-terminal region of L-PGDS by polymerase chain reaction (PCR) in the following manner.

The primer nucleotide sequences used are:
Ec23ALA: Sequence ID NO:1.
78NMUTA: Sequence ID NO:2.

PCR was carried out using Taq DNA polymerase (Takara Shuzo Co., Ltd.), restriction enzymes EcoRI and XhoI, and T4 DNA ligase (Takara Shuzo) where 1 cycle reaction (94° C. for 5 seconds, 45° C. for 3 seconds, and at 72° C. for 5 seconds) was repeated 28 times.

With these primers, the partial nucleotide sequence between the 152 to 327 positions (from guanine (G) to cytosine (C), corresponding to the partial amino acid sequence between the N-terminal (alanine) and the 81 position (serine) on the amino acid sequence of the mature protein excluding its signal sequence) was amplified and an EcoRI site was introduced into the 5'-terminal. Because this PCR product had an XhoI site at the 238 position, the product was subcloned by digestion with restriction enzymes EcoRI and XhoI. A recombinant DNA was obtained by replacement, by the subcloned product, of the corresponding N-terminal region of the cDNA for native L-PGDS (Nagata et al., Proc. Natl. Acad. Sci. USA, 88, 4020–4024 (1991)). This recombinant DNA was inserted into an EcoRI site of vector pGEX-2T (Pharmacia) which was selected for GST fusion protein.

Alternatively, a 521 bp product was obtained by amplifying that region of cDNA coding for the whole mature protein of L-PGDS by PCR as described below.

The primer nucleotide sequences used are:
forward primer: Sequence ID NO:3.
reverse primer: Sequence ID NO:4.

PCR was carried out using Taq DNA polymerase (Takara Shuzo) where 1 cycle reaction (94° C. for 5 seconds, 45° C. for 3 seconds, and at 72° C. for 5 seconds) was repeated 28 times.

With these primers, the region between the 152 to 656 positions (from guanine (G) to adenine (A), corresponding to,the region between the N-terminal (alanine) to the C-terminal (glutamine) of the amino acid sequence of the mature protein excluding its signal sequence) was amplified, and a BamHI site was introduced at the 5'-terminal and an EcoRI site at the 3'-terminal. The amplified DNA was inserted into EcoRI/BamHI sites of vector pGEX-2T (Pharmacia) for GST fusion protein.

The resulting expression vector for GST-L-PGDS fusion protein was transformed in a usual manner into E. coli DH5 α or JM109. The fusion protein produced by the transformant was recovered by selective absorption onto affinity chromatography beads (Pharmacia) and subsequent elution with thrombin according to manufacture's instructions. In this manner, about 2 mg L-PGDS was obtained from 100 ml culture of the transformant.

Proteins produced by 2 independent clones (E. coli DH5α/pGDS2 and E. coli DH5α/pGDS7) were analyzed by SDS-PAGE on 10–20% gradient gel. The results are shown in FIG. 1.

In FIG. 1, lane 1 shows bands of molecular-weight markers; lanes 2 to 5, from one of the above clones; lanes 6 to 9, from the other clone; lanes 2 and 6, homogenates of the respective clones; lanes 3 and 7, fractions not absorbed onto the affinity column; lanes 4 and 8, fractions eluted with thrombin; and lanes 5 and 9, fractions eluted with a buffer containing reduced glutathione. In lanes 2 and 6, a band corresponding to a molecular weight of about 45 kDa is the fusion protein, and this band is scarcely observed in the GST-unbound fractions (lanes 3 and 7). The fractions eluted with glutathione (lanes 5 and 9) showed the fusion protein band and GST band (molecular weight of about 25 kDa), which were not eluted with thrombin.

According to these results in SDS-PAGE, L-PGDS was produced in E. coli in the form of an about 45 kDa fusion protein with GST, and the protein with a molecular weight of about 20 kDa, eluted with thrombin (lanes 4 and 8), is L-PGDS itself because this molecular weight corresponds to the molecular weight of 20 kDa deduced from the nucleotide sequence for L-PGDS.

(2) Preparation of the Antibody-producing Cells

A 0.5 ml solution containing 500 µg L-PGDS obtained in (1) was mixed with 0.5 ml Freund complete adjuvant and emulsified for 3 to 5 minutes. As antigen, 100µl of the emulsion was administrated by s.c. into the tail rump of a BALB/c mouse. 3 weeks after the first immunization, the same volume of another antigen emulsion in Freund incomplete adjuvant was administrated by i.p. to the mouse for boosting. 3 weeks after the second immunization, 100 µg antigen (100µg antigen/200 µl PBS) was administrated to each mouse via its tail vein. 3 days after the final immunization, the spleen was excised from the immunized mouse and disrupted in E-RDF medium to give a cell suspension.

(3) Cell Fusion

The suspended 1×10$^8$ spleen cells were subject to cell fusion with 1×10$^7$ mouse myeloma cells P3-X63-Ag8-U1 (P3-U1) or P3-X-63-Ag8.653 in 50% (W/V) PEG (molecular weight 1,500, Boehringer Mannheim) according to the method of Oi and Herzenberg (Selected Methods in Cellular Immunology, 351–371, W. H. Freeman Co., USA press, 1980).

(4) Selection of the Hybridoma

According to the above-mentioned method of Oi et al., the desired hybridoma was selected in HAT medium, i.e. E-RDF medium containing 1.36 mg/dl hypoxanthine, 19.1 µg/dl aminopterin, 387 µg/dl thymidine, 10% fetal bovine serum and 5% Origen HCF (IGEN).

(5) Selection of the Monoclonal Antibodies

The antibody-positive cells in 15 wells were cloned by repeating limiting dilution at least twice. The resulting 6 clones were cultured to give strains producing a significant amount of the monoclonal antibody specific to L-PGDS, as follows:

1×10$^7$ hybridoma cells were cultured at 37° C. for 4 days in 5% CO$_2$ in the 225 cm$^2$ flask containing 50 ml E-RDF medium with 10% fetal calf serum. Among the resulting 6 cell lines, 5 lines were selected. The results are shown in Table 1.

TABLE 1

| Antigen | number of total wells | number of cell growth wells | number of antibody-positive wells | number of antibody established wells |
|---|---|---|---|---|
| hPGDS | 960 | 778 | 15 | 6 | hPGDS: human lipocalin-type prostaglandin D synthase.

In Table 1, "number of cell growth wells" means the number of wells where hybridomas could grow in selective culture in HAT medium; "number of antibody-positive wells", the number of wells where antibody production was detected by ELISA using the antigen prepared in Example 1 (1); and "number of antibody established wells", the number of wells where hybridomas producing the specific antibody were established by cloning. The 5 selected cell lines were designated 1B7, 6F5, 7F5, 9A6 and 10A3, respectively. The antibodies produced by these cell lines were given the same designations as above. The cell lines 1B7, 6F5, 7F5, 9A6 and 10A3 have been deposited as FERM BP-5709 (original, deposit date: Sept. 21, 1995), FERM BP-5710 (original deposit date: Sept. 21, 1995), FERM BP-5711 (original deposit date: Jun. 6, 1996), FERM BP-5712 (original deposit date: Jun. 6, 1996) and FERM BP-5713 (original deposit date: Jun. 6, 1996), respectively, with National Institute of Bioscience and Human-Technology, Agency of Industrial Science and Technology (Higashi 1-1-3, Tsukuba City, Ibaragi Pref., Japan).

(6) Production of the Monoclonal Antibodies

Each of the cell lines 1B7, 6F5, 7F5, 9A6 and 10A3, selected above in (5), was administrated by i.p. to mice. Remaining resulting cell strain, 6B9 was also administrated by i.p. to mice. Briefly, 1 ml pristane was administrated by i.p. to each mouse. 2 weeks thereafter, $1 \times 10^8$ hybridoma cells were inoculated intraperitoneally the mouse, and 2 weeks thereafter, the transuded ascites was collected from the mouse.

The collected ascites was applied to Protein A affinity column chromatography according to a conventional method.

As a result, 3 to 10 mg/ml antibodies against L-PGDS were obtained.

Typing of the antibodies of 1B7, 6F5 with Isotyping Kit (RPN29, AMERSHAM) indicated that all of them belong to IgG1 subclass and possess λ light chain.

EXAMPLE 2

Properties of the Monoclonal Antibodies (1) Specificity Examination by ELISA

A 96-well microtiter plate was coated with various types of L-PGDS and blocked with 0.2% gelatin in PBS. After blocking, each of the 6 antibodies obtained in Example 1 (5 was examined for specificity in ELISA after adding 50 μl antibody solution to each well. The results are shown in Table 2.

TABLE 2

| antigen | 1B7 | 6B9 | 6F5 | 7F5 | 9A6 | 10A3 |
|---|---|---|---|---|---|---|
| E. coli antigen | O | O | O | O | O | O |
| E. coli lysate | X | X | X | X | X | X |
| CHO antigen | O | O | O | O | X | O |
| CSF antigen | O | O | O | X | X | X |

O: Reactivity was observed. X: No reactivity was observed.

The antigens in the table are as follows:

*E. coli* antigen, expressed in *E. coli* and purified by affinity chromatography;

*E. coli* lysate, carrying a vector not containing L-PGDS cDNA (negative control);

CHO antigen, expressed in CHO cells and purified by a conventional method; and

CSF antigen, purified from CSF by a conventional method.

The results in Table 2 suggested that at least 3 antibodies 1B7, 6B9 and 6F5 specifically recognize L-PGDS itself.

(2) Specificity Examination by Western Blotting

The above antigens were electrophoresed by SDS-PAGE on 16% isocratic gel and then subjected to Western blot analysis using 5 kinds of antibody. The results are shown in Table 3.

TABLE 3

| antigens | 1B7 | 6B9 | 6F5 | 9A6 | 10A3 |
|---|---|---|---|---|---|
| E. coli antigen | O | O | O | O | O |
| E. coli lysate | X | X | X | X | X |
| CHO antigen | O | O | O | X | O |

O: A signal was observed. X: No signal was observed.

A signal, appearing in an immunoblot profile obtained in coloration after Western blotting, was detected at a position corresponding to the molecular weight (about 20 to 30 kDa) of prostaglandin D synthase. Hence, the antigens showing such signals are considered specific to prostaglandin D synthase.

Figure 2:
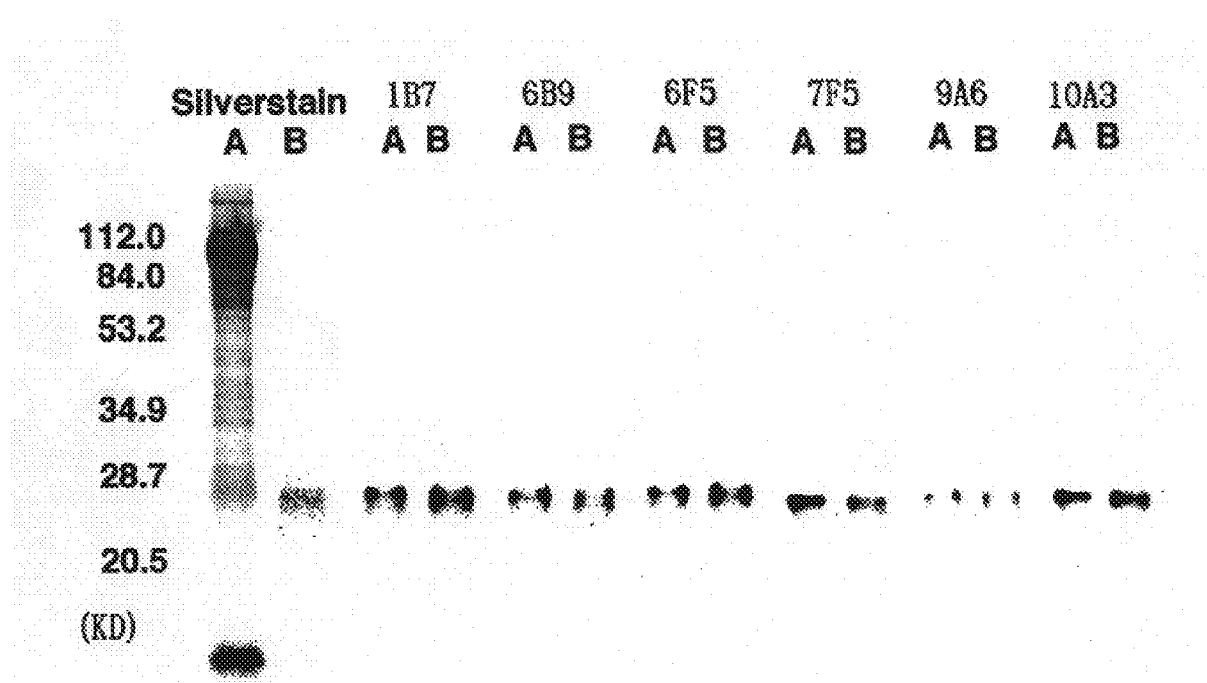
FIG. 2 is a photograph showing a profile in SDS-PAGE and Western blotting of CSF and purified L-PGDS.

FIG. 2 shows the results of Western blot analysis using CSF antigen and CSF itself.

Each lane A shows CSF where 2 μl was applied. Each lane B shows L-PGDS (CSF antigen) purified from CSF where 50 ng was applied. Silver staining indicated a large number of proteins in CSF, and the purified L-PGDS appears as a broad band with a molecular weight of about 27 kD.

Each monoclonal antibody was used in Western blotting. The results revealed that all monoclonal antibodies (1B7, 6B9, 6F5, 7F5, 9A6 and 10A3) are reactive exclusively to the single protein (lane A) corresponding to the purified L-PGDS (lane B), indicating that these antibodies specifically recognize L-PGDS without reacting to other contaminants in CSF.

Figure 3:
FIG. 3 is a photograph showing a profile in Western blotting of purified L-PGDS treated with N-glycanase.

In addition, the purified L-PGDS was treated with N-glycanase and then subjected to Western blot analysis. The results are shown in FIG. 3. Each lane A shows the sample treated with glycanase, and each lane B shows the sample not treated with glycanase. As shown in FIG. 3, there is no significant difference in band density before and after treatment with glycanase in the case of 1B7, 6B9, 6F5, 7F5, and 1A3, while in the case of 9A6, the intensity of the band was significantly increased after treatment with glycanase, suggesting that 9A6 recognizes a glycosylation site or therearound.

Then, the isotype of each monoclonal antibody was determined using a mouse monoclonal antibody typing kit (RPN29, Amersham). The results are shown in Table 4. Further, their Kd values toward the *E. coli* antigen and CSF antigen were determined by the method of Friguet et al. (J. Immunol. Methods, 77, 305–319 (1985)). The results are shown in Table 4.

TABLE 4

| monoclonal antibody | immunoglobulin subclass | dissociation constant (nM) | |
|---|---|---|---|
| | | E. coli antigen | CSF antigen |
| 1B7 | IgG$_1$ (λ) | 5.4 | 3.9 |
| 6B9 | IgG$_1$ (κ) | >1000 | >1000 |
| 6F5 | IgG$_1$ (λ) | 13.2 | 10.3 |
| 7F5 | IgG$_1$ (κ) | 0.65 | 4.1 |
| 9A6 | IgG$_{2a}$ (κ) | 7.42 | >1000 |
| 10A3 | IgG$_1$ (κ) | 0.53 | 3.9 |

1B7, 6F5, 7F5 and 10A3 showed high affinities for the *E. coli* antigen and CSF antigen, indicating that these monoclonal antibodies recognize the surface of native L-PGDS molecule. 9A6 showed a high affinity for the *E. coli* antigen, but it showed least reactivity to the CSF antigen. The results, along with these results in FIG. 3, suggested that 9A6 recognizes a glycosylation or therearound. 6B9 showed reactivity in Western blotting as shown in FIG. 2, but showed no reactivity to the *E. coli* antigen or the CSF antigen, suggesting its recognition of the denatured molecule of L-PGDS.

Then, deletion mutants of L-PGDS were prepared by truncation of its partial N-terminal amino acid sequence step by step and used as antigens for epitope mapping of their monoclonal antibodies. The PCR primers used in this experiment are shown below and the results are shown in FIG. 4. The antigens used in this experiment were prepared in essentially the same way as in Example 1(1) except that the L-PGDS product was recovered in the form of a fusion protein with GST by boiling in 1% SDS, not by treatment with thrombin.

forward primer A (amino acids 1 to 7): SEQ ID NO:3.
forward primer B (amino acids 7 to 12): SEQ ID NO:5.
forward primer C (amino acids 13 to 18): SEQ ID NO:6.
forward primer D (amino acids 30 to 35): SEQ ID NO:7.
forward primer E (amino acids 52 to 57): SEQ ID NO:8.
forward primer F (amino acids 68 to 73): SEQ ID NO:9.
forward primer G (amino acids 85 to 90): SEQ ID NO:1.
forward primer H (amino acids 99 to 105): SEQ ID NO:11.
forward primer I (amino acids 118 to 123): SEQ ID NO:12.
forward primer J (amino acids 134 to 139): SEQ ID NO:13.
forward primer K (amino acids 152 to 158): SEQ ID NO:14.
reverse primer (amino acids 163 to 168): SEQ ID NO:4.

Figure 5:
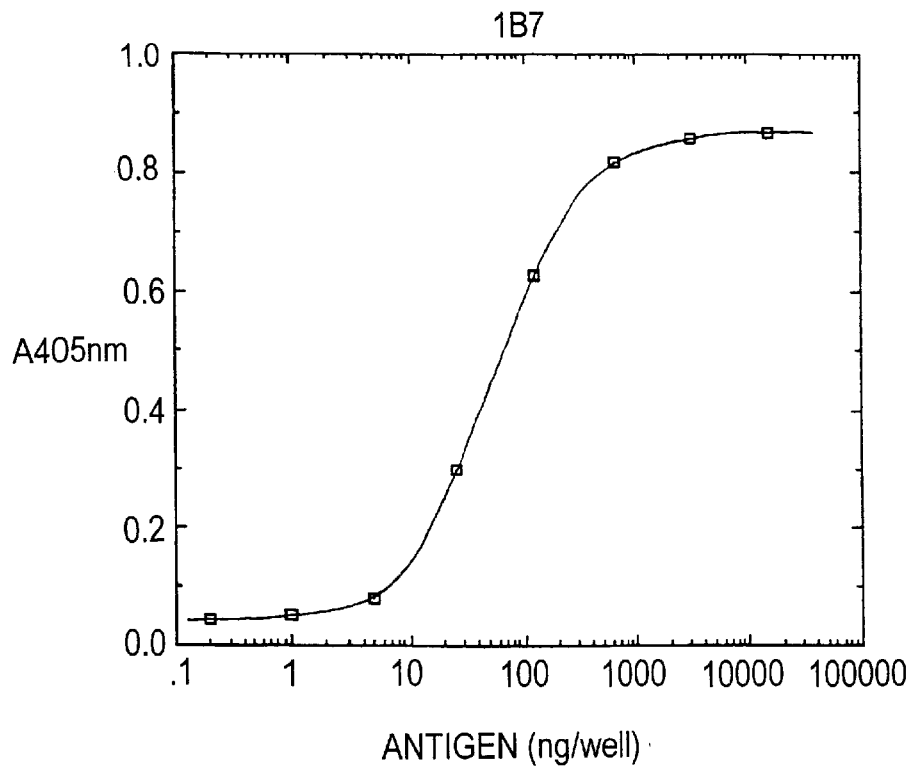
FIG. 5 is a calibration curve for L-PGDS (by monoclonal antibody 1B7).
Figure 6:
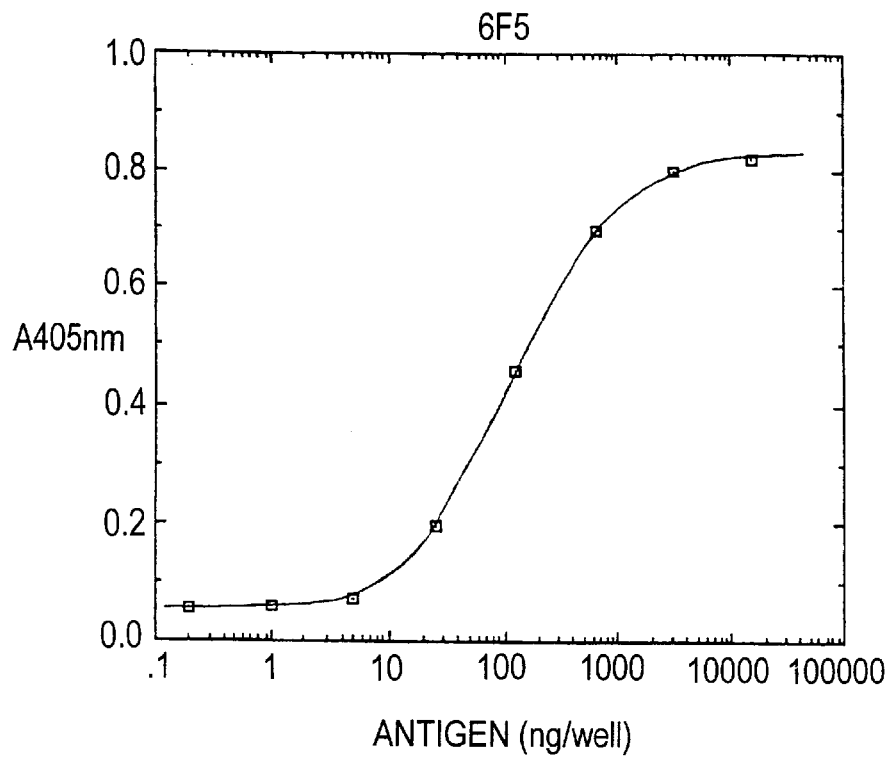
FIG. 6 is a calibration curve for L-PGDS (by monoclonal antibody 6F5).

FIG. 4 suggested that 7F5 and 10A3 recognize a sequence in $Ala^1$-$Val^6$; 9A6, $Gln^{13}$-$Asn^{29}$; 6F5, $Tyr^{85}$-$Val^{98}$; and 1B7 and 6B9, $Gly^{118}$-$Pro^{133}$ (3) Preparation of Calibration Curves The above *E. coli* antigen was used for preparation of calibration curves for L-PGDS. The monoclonal antibodies used were 1B7 and 6F5. A 96-well microtiter plate was coated with diluted *E. coil* antigen and blocked with 0.2% gelatin in PBS. After blocking, the biotinylated monoclonal antibody 1B7 or 6F5 was added to each well and incubated. Then, the plate was washed, and a streptoavidin-horseradish peroxidase conjugate was added to each well and incubated. The plate was washed, and a coloration substrate ABTS (2,2'-azino-di-(3-ethyl-benzothiazoline-6-sulfonic acid) was added to each well. L-PGDS was determined by measuring this coloration by the calorimetric method. The results are shown in FIGS. 5 and 6 for 1B7 and 6F5, respectively.

Figure 7:
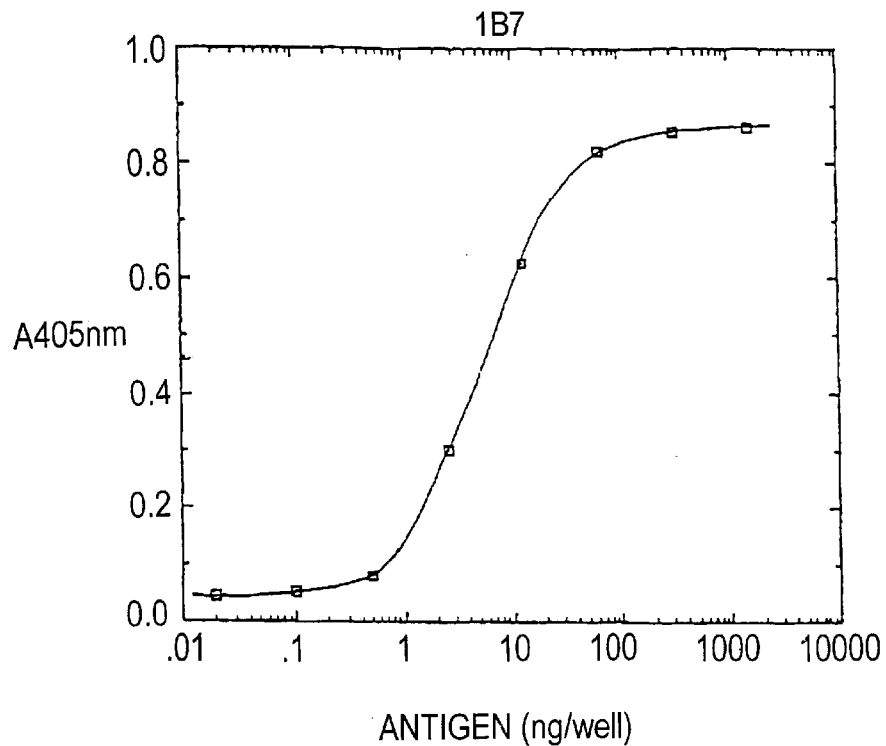
FIG. 7 is a calibration curve for L-PGDS (by sandwich ELISA method using monoclonal antibody 1B7 as primary antibody and biotinylated polyclonal antibody as secondary antibody).
Figure 8:
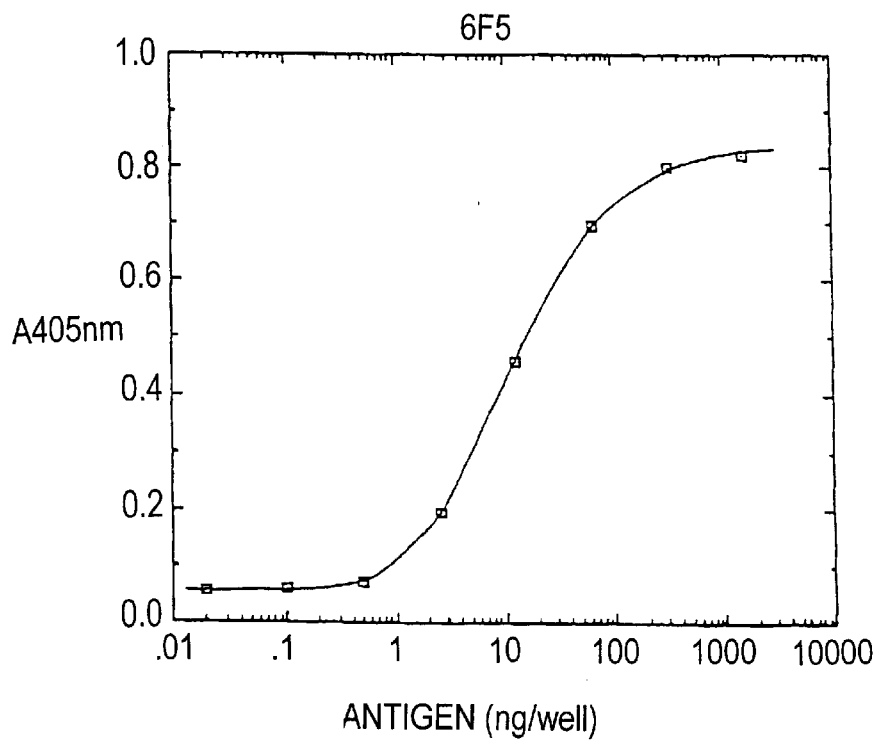
FIG. 8 is a calibration curve for L-PGDS (by sandwich-ELISA method using monoclonal antibody 6F5 as primary antibody and biotinylated polyclonal antibody as secondary antibody).

Then, the sandwich ELISA method was used for calibration curves for L-PGDS. A 96-well microtiter plate was coated with diluted monoclonal antibody 1B7 or 6F5 and blocked with 0.2 % gelatin in PBS. After blocking, the diluted *E. coli* antigen was added to each well and incubated. Then, the plate was washed, and the biotinylated polyclonal antibody was added to each well and incubated. Then, the plate was washed, and a streptoavidin-horseradish peroxidase conjugate was added to each well and incubated. The plate was washed, and a coloration substrate ABTS (2,2'-azino-di-(3-ethyl-benzothiazoline-6-sulfonic acid) was added to each well. L-PGDS was determined by measuring this coloration by the colorimetric method. The results are shown in FIGS. 7 and 8 for 1B7 and 6F5, respectively. As can be seen from FIGS. 5 to 8, about 10-fold higher sensitivity was attained using the sandwich ELISA method.

In another embodiment of the present invention, the sandwich ELISA method and the biotinylated polyclonal or monoclonal antibody were used for preparation of calibration curves. A 96-well microtiter plate was coated with diluted monoclonal antibody 1B7, 10A3 or 7F5 as primary antibody and blocked with 0.2% gelatin in PBS. The diluted *E. coli* antigen was then added to each well and incubated. Then, the plate was washed, and the biotinylated polyclonal antibody or the biotinylated monoclonal antibody 1B7, 7F5 or 10A3 was added as secondary antibody to each well and incubated. The plate was washed, and a streptoavidin-horseradish peroxidase conjugate was added to each well and incubated. The plate was washed, and a coloration substrate ABTS (2,2'-azino-di-(3-ethyl-benzothiazoline-6-sulfonic acid) was added to each well. L-PGDS was determined by measuring this coloration by the calorimetric method.

Figure 9:
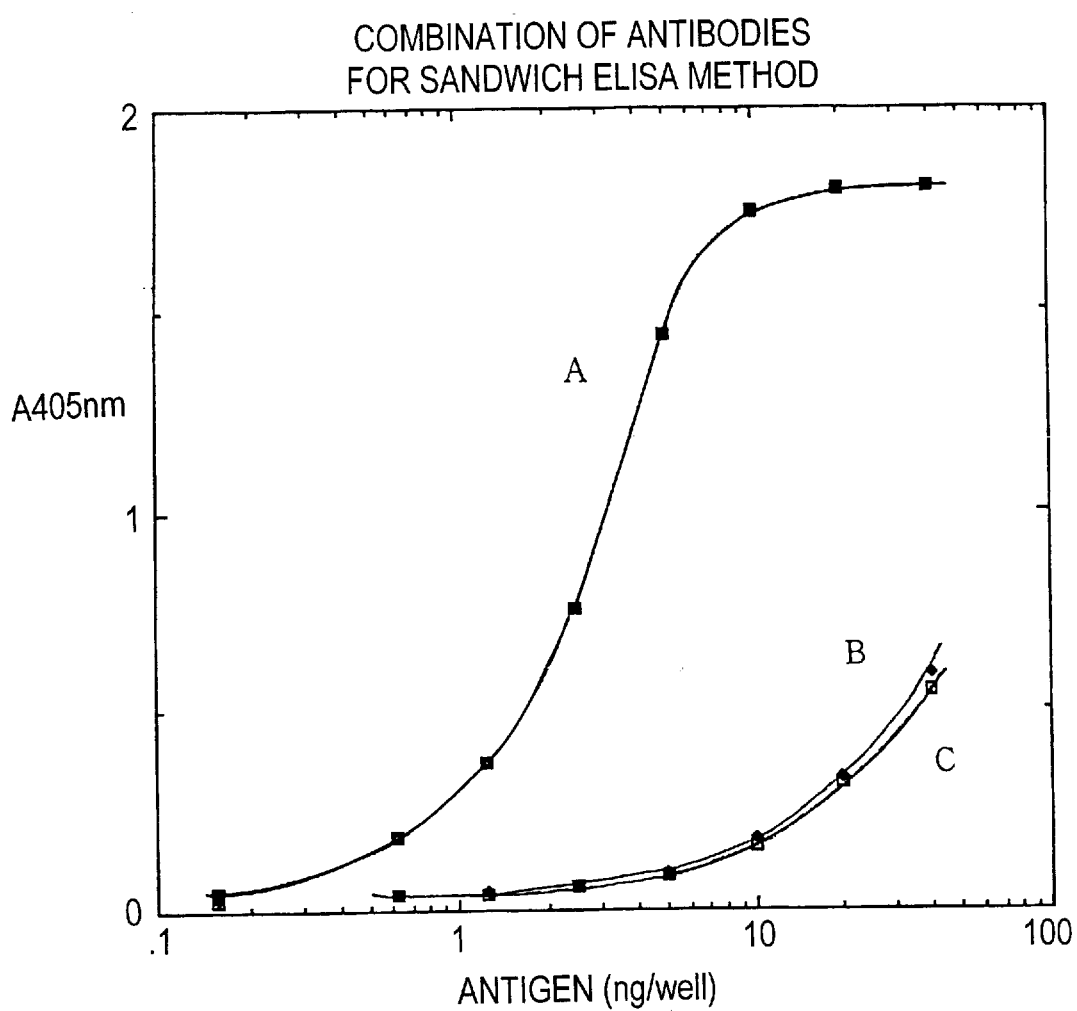
FIG. 9 is a calibration curve for L-PGDS (by sandwich ELISA method using monoclonal antibody 1B7 as primary antibody and biotinylated polyclonal antibody (A), biotinylated 7B5 (B) and biotinylated 10A3 (C) as secondary antibodies).
Figure 10:
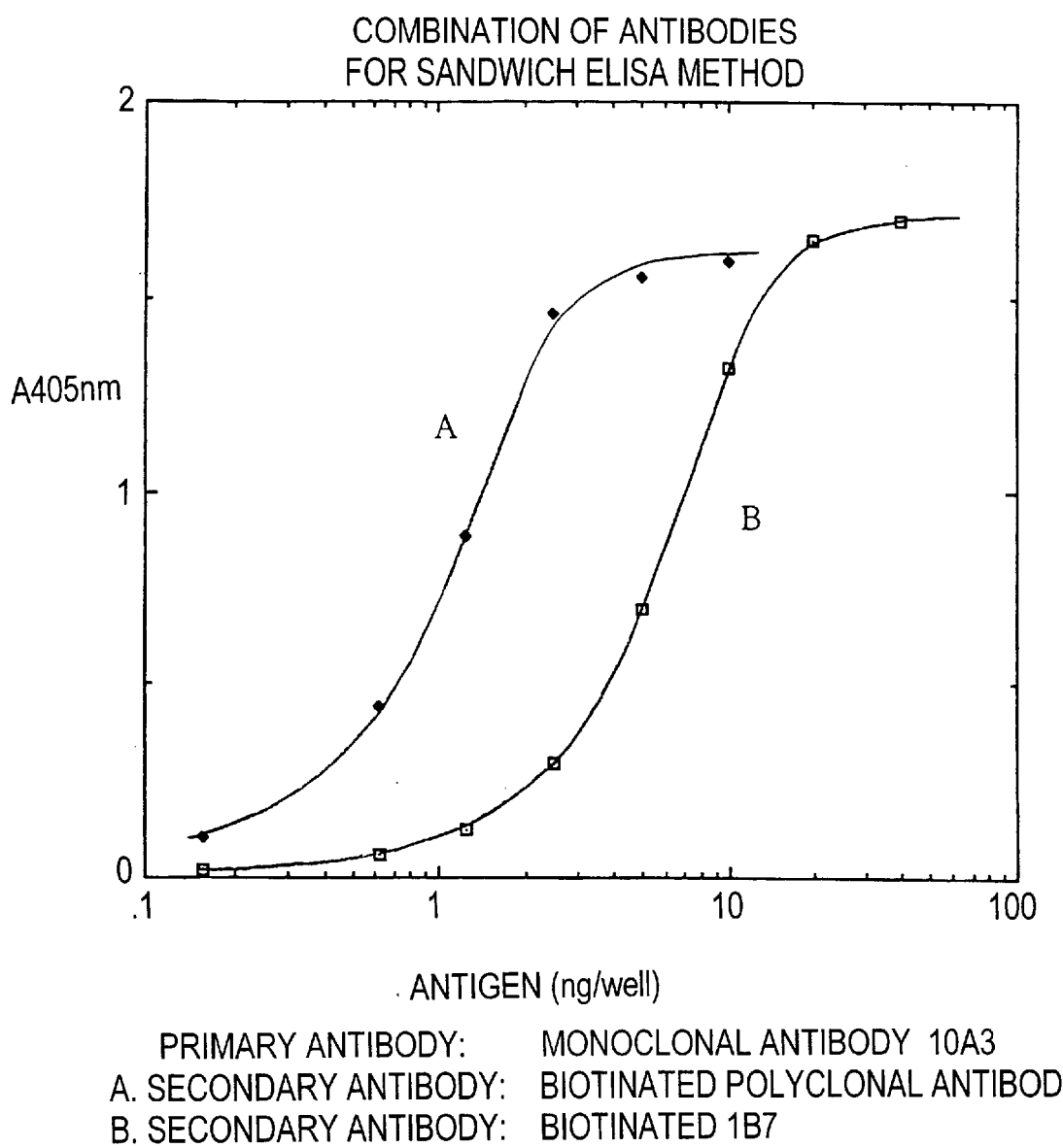
FIG. 10 is a calibration curve for L-PGDS (by sandwich ELISA method using monoclonal antibody 10A3 as primary antibody and biotinylated polyclonal antibody (A) and biotinylated 1B7 (B) as secondary antibodies).
Figure 11:
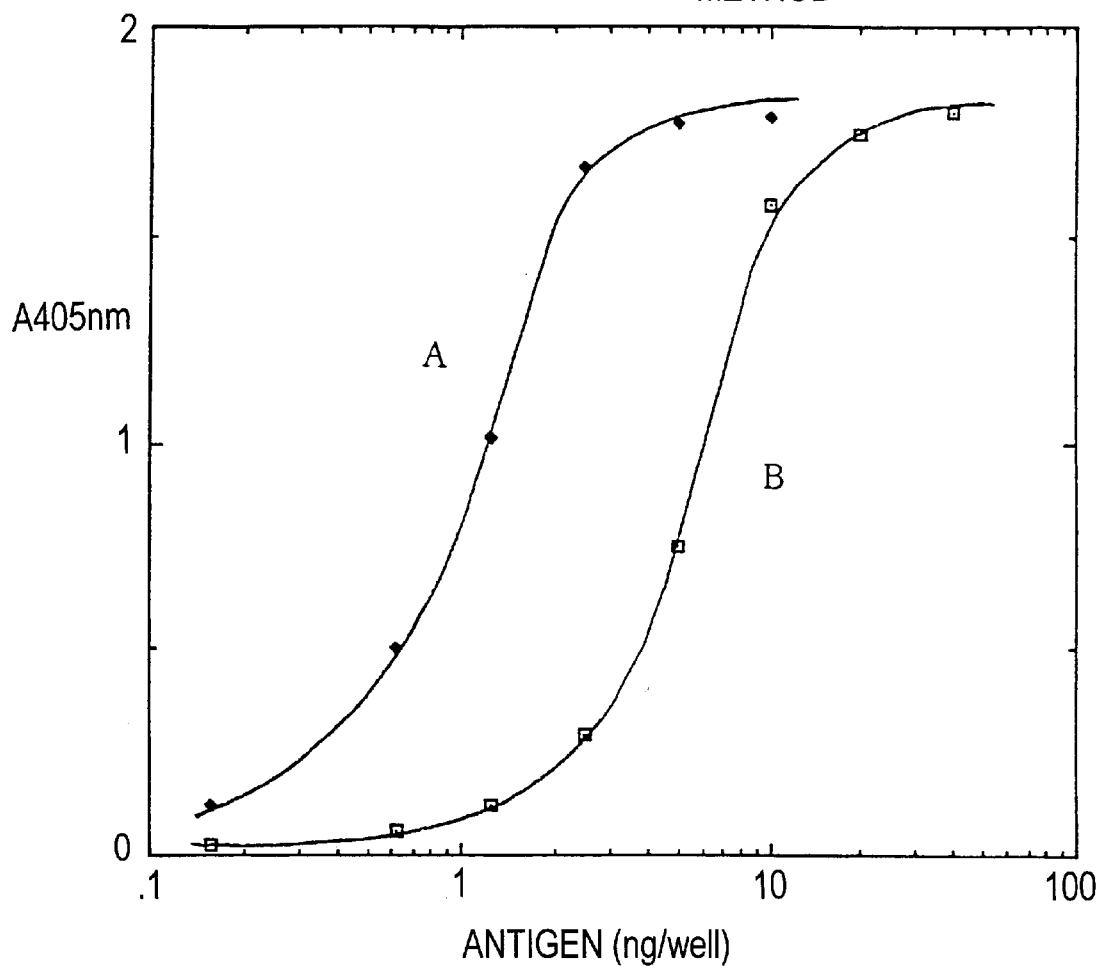
FIG. 11 is a calibration curve for L-PGDS (by sandwich ELISA method using monoclonal antibody 7F5 as primary antibody and biotinylated polyclonal antibody (A) and biotinylated 1B7 (B) as secondary antibodies).

The results are shown in FIGS. 9 to 11.

FIG. 9 shows the calibration curves using monoclonal antibody 1B7 as primary antibody, where curve A makes use of the biotinylated polyclonal antibody as secondary antibody; curve B, biotinylated 7F5 as secondary antibody; and curve C, biotinylated 10A3 as secondary antibody.

FIG. 10 shows the resulting calibration curves using monoclonal antibody 10A3 as primary antibody, where curve A makes use of the biotinylated polyclonal antibody as secondary antibody; and curve B, biotinylated 1B7 as secondary antibody.

FIG. 11 shows the calibration curves using monoclonal antibody 7F5 as primary antibody, where curve A makes use of the biotinylated polyclonal antibody as secondary antibody; and curve B, biotinylated 1B7 as secondary antibody.

As can be seen from FIGS. 9 to 11, high sensitivity can be attained using 10A3 or 7F5 as primary antibody and the biotinylated polyclonal antibody, or biotinylated monoclonal antibody 1B7, as secondary antibody.

EXAMPLE 3

Detection of L-PGDS Derived From Various Human Tissues (1) Detection of L-PGDS in CSF A 96-well microtiter plate was coated with diluted monoclonal antibody 1B7 or 6F5 and then blocked with 0.2% gelatin in PBS. Diluted human CSF was then added to each well and incubated. Separately, the polyclonal antibody prepared using a rabbit as an immunized animal was purified by affinity column chromatography on Protein A and then biotinylated with NHS-LC-Biotinylation Kit (PIERCE).

Subsequently, the above microtiter plate was washed, and the biotinylated polyclonal antibody was added to each well and then incubated. Subsequently, a streptoavidin-horseradish peroxidase conjugate was added to each well and incubated. The plate was washed, and a coloration substrate ABTS (2,2'-azino-di-(3-ethyl-benzothiazoline-6-sulfonic acid) was added to each well. L-PGDS was determined by measuring this coloration by the calorimetric method. The results are shown in Table 5.

TABLE 5

| Sample No. | 1 | 2 | 3 | 4 | 5 |
|---|---|---|---|---|---|
| L-PGDS (µg/ml) | 23 | 31 | 20 | 10 | 18 |

(2) Detection of L-PGDS in blood

L-PGDS in human serum obtained by centrifugation of human blood was determined by the same method as in (1) above except that diluted serum was used. The results are shown in Table 6.

TABLE 6

| Sample No. | 1 | 2 | 3 | 4 | 5 |
|---|---|---|---|---|---|
| L-PGDS ($\mu$g/ml) | 0.45 | 0.29 | 0.21 | 0.41 | 0.26 |

(3) Detection of L-PGDS in amniotic fluid

L-PGDS in human amniotic fluid was determined by the same method as (1) above except that diluted amniotic fluid was used. The results are shown in Table 7.

TABLE 7

| Sample No. | 1 | 2 | 3 | 4 | 5 |
|---|---|---|---|---|---|
| L-PGDS ($\mu$g/ml) | 5.5 | 1.2 | 1.3 | 2.9 | 1.8 |

(4) Detection of L-PGDS in semen supernatant

L-PGDS in human seminal plasma was determined by the same method in (1) above except that diluted seminal plasma was used. The results are shown in Table 8.

TABLE 8

| Sample No. | 1 | 2 | 3 | 4 | 5 |
|---|---|---|---|---|---|
| L-PGDS ($\mu$g/ml) | 4.1 | 12 | 23 | 10 | 8.3 |

(5) Detection of L-PGDS in follicular fluid

L-PGDS in human follicular fluid was determined by the same method in (1) above except that diluted follicular fluid was used. The results are shown in Table 9.

TABLE 9

| Sample No. | 1 | 2 | 3 | 4 | 5 |
|---|---|---|---|---|---|
| L-PGDS ($\mu$g/ml) | 0.21 | 0.11 | 0.11 | 0.15 | 0.13 |

(6) Detection of L-PGDS in urine

L-PGDS in human urine was determined by the same method in (1) above except that diluted urine was used. The results are shown in Table 10.

TABLE 10

| Sample No. | 1 | 2 | 3 | 4 | 5 |
|---|---|---|---|---|---|
| L-PGDS ($\mu$g/ml) | 1.07 | 0.65 | 2.45 | 1.62 | 0.32 |

(7) Detection of L-PGDS in various humors

The sandwich ELISA system (7F5 monoclonal antibody× biotinylated 1B7 monoclonal antibody) established in Example 2(3) was used for quantifying L-PGDS in human CSF, serum and urine. The results (means (±SE)) were compared with those of previous literatures. In this assay, TMBLUE (Intergen-CDP) was used as colouring substrate in place of ABTS.

The measurement means are shown in Table 11.A, and those of the literatures are shown in Table 11.B. L-PGDS levels in amniotic fluid and seminal plasma were also determined in the same manner, and the results (means (±SE)) are shown in Table 11.A, as well.

TABLE 11.A

| sample | number of samples | means (±SE) ($\mu$g/ml) |
|---|---|---|
| CSF | 38 | 12.07 ± 1.26 |
| serum | 12 | 0.27 ± 0.01 |
| urine | 10 | 1.56 ± 0.30* |
| amniotic fluid | 52 | 2.55 ± 0.22 |
| seminal plasma | 32 | 13.01 ± 1.72 |

*Excretion amount (mg) per day

TABLE 11.B

| sample | number of samples | means (±SD) ($\mu$g/ml) | literature |
|---|---|---|---|
| CSF | 12 | 40 | Pepe, A. J. and Hochwald, G. M. (1967) Proc. Soc. Exp. Biol. 126, 630–633 |
| CSF | 59 | 26(±6) | Link, H. and Olsson, J. E. (1972) Acta Neurol. Scadinav. 48, 57–68 |
| CSF | 35 | 27(±1.5) | Olsson, J. E., Link, H., and Müller, R. (1976) J. Neurol. Sci. 27, 233–245 |
| CSF | 192 | 33(±11) | Felgenhauer, K., Schadlich, H. J., and Nekic, M. (1987) Klin. Wochenschr. 65, 764–768 |
| serum | 25 | 3.9(±0.16) | Olsson, J. E., Link, H., and Nosslin, B. (1973) J. Neurochem. 21, 1153–1159 |
| urine | 15 | 3.6~53.9* | Whitsed, H. and Penny, R. (1974) Clin. Chim. Acta 50, 119–128 |

*Excretion amount (mg) per day (not mean).

As shown in the tables, the present means are lower than those of the literatures, particularly with respect to serum considered to have contaminants in abundance. This difference may result from the fact that L-PGDS might be overestimated in the methods of the literatures because of their low specificity, and high specificity in the present assay system is clarified.

Figure 12:
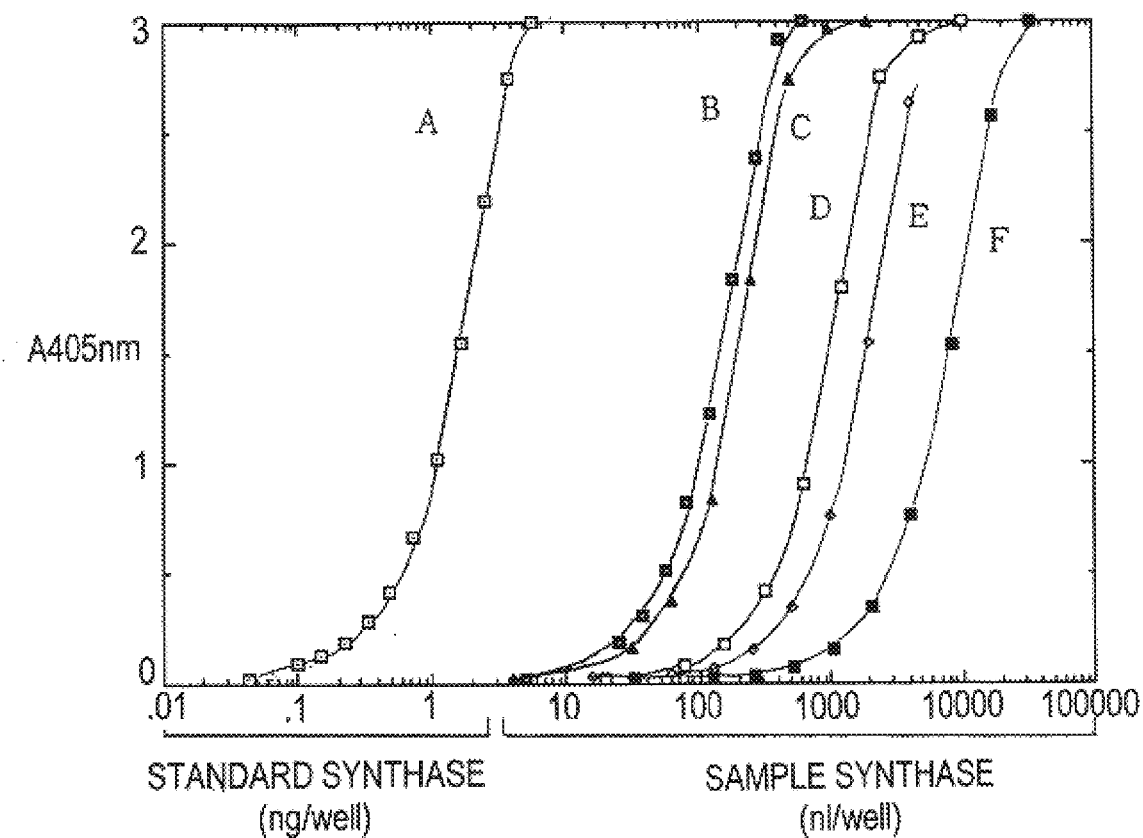
FIG. 12 is a drawing showing a calibration curve prepared using L-PGDS and calibration curves for L-PGDS which were prepared using several samples.

A typical calibration curve prepared in these measurements is shown in FIG. 12.

Curve A is a calibration curve where L-PGDS purified from CSF or the recombinant L-PGDS prepared in Example 1(1) was used as the standard substance. Curves B, C, D, E, and F are calibration curves prepared using CSF, seminal plasma, urine, amniotic fluid, and serum, respectively. As can be seen from FIG. 12, the sample calibration curves are nearly parallel with the calibration curve A, so L-PGDS can be specifically determined in the present assay system without any influence of contaminants in a sample.

Then, an additive test in the present assay system was carried out. Human CSF, serum, urine, and seminal plasma were diluted respectively to adjust their L-PGDS contents to about 20 ng/ml. Purified L-PGDS (CSF antigen) from CSF was added in an amount of 15 ng/ml to each sample. The results indicated that good recovery (98.5 to 104.6%) was obtained in every sample as shown in Table 12.

TABLE 12

| sample | dilution degree (-fold) | L-PGDS (ng/ml) initial conc. | addition | recovery | recovery (%) |
|---|---|---|---|---|---|
| CSF 1 | 350 | 20.69 | 15.00 | 35.65 | 99.7 |
| CSF 2 | 600 | 21.17 | 15.00 | 36.31 | 100.9 |
| serum 1 | 15 | 20.71 | 15.00 | 36.21 | 103.3 |
| serum 2 | 15 | 18.67 | 15.00 | 33.96 | 101.9 |
| urine 1 | 40 | 20.86 | 15.00 | 36.55 | 104.6 |
| urine 2 | 40 | 18.56 | 15.00 | 33.34 | 98.5 |
| seminal plasma 1 | 500 | 16.82 | 15.00 | 31.70 | 99.2 |
| seminal plasma 2 | 1000 | 19.51 | 15.00 | 34.93 | 102.8 |

EXAMPLE 4

Figure 13:
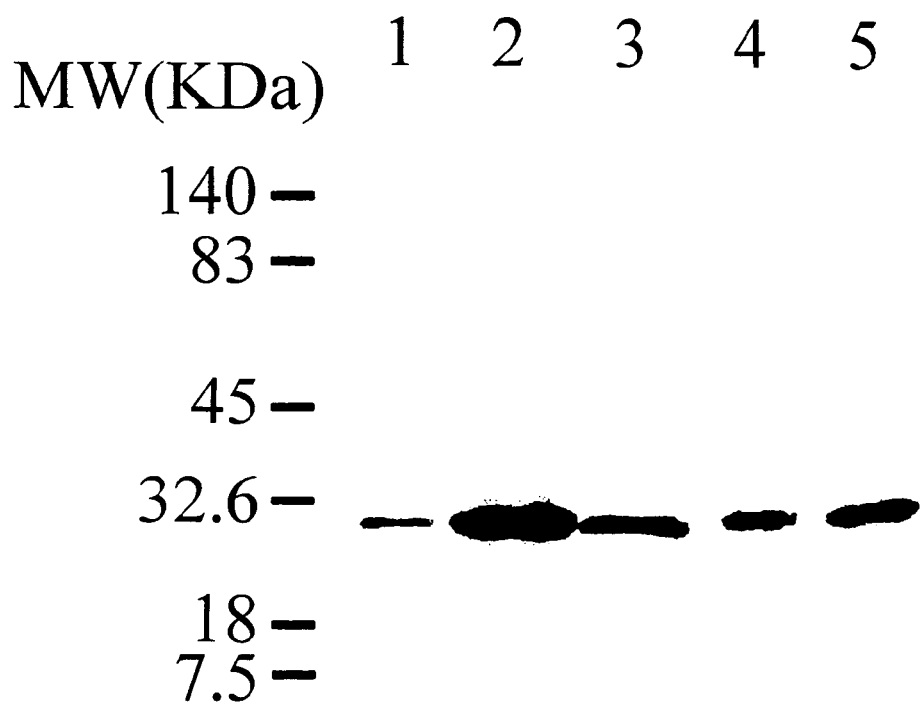
FIG. 13 is a photograph showing a profile in Western blotting.

L-PGDS in 5 samples (seminal plasma) was detected by Western blotting using the monoclonal antibody 1B7. The results are shown in FIG. 13. As shown in FIG. 13, L-PGDS was detected specifically, indicating that this monoclonal antibody is reactive exclusively to L-PGDS in the presence of other contaminants.

Then, the sandwich ELISA system (monoclonal antibody 1B7×biotinated polyclonal antibody) established in Example 2 was used to quantify L-PGDS in 1 ml seminal plasma from each of healthy normal persons (40 cases) and patients with oligospermia (10 cases). The number of spermatozoa in 1 ml semen was determined with a Makler counting chamber. The results are shown in Table 13.

TABLE 13

| sample no. | number of spermatozoa ($\times 10^4$ spermatozoa/ml) | subject | L-PGDS ($\mu$g/ml) by ELISA |
|---|---|---|---|
| 1 | 0 | oligospermia patient | 2.6 |
| 2 | 100 | oligospermia patient | 0.8 |
| 3 | 100 | oligospermia patient | 1.0 |
| 4 | 800 | oligospermia patient | 3.8 |
| 5 | 800 | oligospermia patient | 2.2 |
| 6 | 1000 | oligospermia patient | 0.9 |
| 7 | 1800 | oligospermia patient | 1.0 |
| 8 | 2000 | oligospermia patient | 5.0 |
| 9 | 2000 | oligospermia patient | 4.8 |
| 10 | 2000 | oligospermia patient | 2.6 |
| 11 | 2500 | healthy person | 4.3 |
| 12 | 3000 | healthy person | 7.5 |
| 13 | 3000 | healthy person | 23.6 |
| 14 | 3000 | healthy person | 30.0 |
| 15 | 3000 | healthy person | 9.5 |
| 16 | 3000 | healthy person | 2.5 |
| 17 | 3000 | healthy person | 4.4 |
| 18 | 4000 | healthy person | 6.0 |
| 19 | 4000 | healthy person | 30.0 |
| 20 | 4200 | healthy person | 8.0 |
| 21 | 5000 | healthy person | 1.9 |
| 22 | 6000 | healthy person | 42.0 |
| 23 | 6000 | healthy person | 1.5 |
| 24 | 6000 | healthy person | 3.8 |
| 25 | 6500 | healthy person | 2.0 |
| 26 | 7000 | healthy person | 3.2 |
| 27 | 7000 | healthy person | 8.2 |
| 28 | 8000 | healthy person | 9.6 |
| 29 | 8000 | healthy person | 14.0 |
| 30 | 8500 | healthy person | 6.0 |
| 31 | 8800 | healthy person | 3.0 |
| 32 | 9000 | healthy person | 8.0 |
| 33 | 9000 | healthy person | 7.1 |
| 34 | 10000 | healthy person | 10.1 |
| 35 | 10000 | healthy person | 3.0 |
| 36 | 10000 | healthy person | 7.5 |
| 37 | 10000 | healthy person | 6.0 |
| 38 | 11000 | healthy person | 0.3 |
| 39 | 12000 | healthy person | 17.0 |
| 40 | 12000 | healthy person | 2.6 |
| 41 | 12000 | healthy person | 7.0 |
| 42 | 12000 | healthy person | 1.1 |
| 43 | 13000 | healthy person | 10.5 |
| 44 | 13900 | healthy person | 30.0 |
| 45 | 15000 | healthy person | 16.0 |
| 46 | 15000 | healthy person | 5.1 |
| 47 | 15000 | healthy person | 3.5 |
| 48 | 16000 | healthy person | 13.0 |
| 49 | 17400 | healthy person | 15.0 |
| 50 | 18000 | healthy person | 6.2 |

Figure 14:
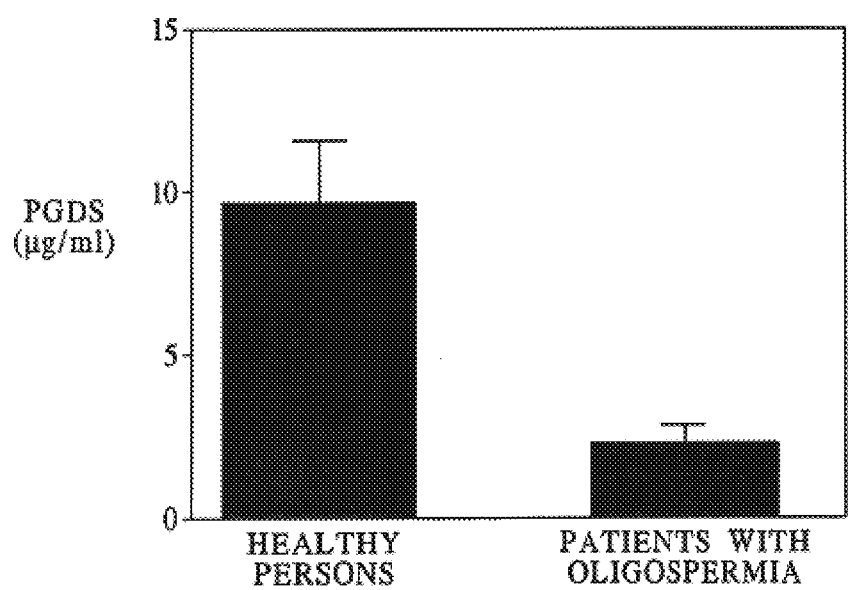
FIG. 14 shows the result of measurement of L-PGDS.

The results indicated that L-PGDS levels are 9.75±1.486 $\mu$g/ml healthy persons) and 2.470±0.509 $\mu$g/ml (oligospermia patients), and the difference therebetween is statistically significant at $P \leq 0.0008$ level (Mann-Whitney method) or $P \leq 0.0192$ (Fisher method), in FIG. 14. Because many samples can be dealt with in a short time using the kit of the present invention, it is useful for diagnosis of oligospermia.

EXAMPLE 5

One-step purification of L-PGDS from CSF was attempted by coupling each of monoclonal antibodies 1B7, 6F5, 9A6, 7F5 and 10A3 to carriers by use of an Affi-Gel Hz immunoaffinity kit (Bio-Rad).

First, 10 ml gel with each monoclonal antibody coupled thereto was equilibrated with PBS. A CSF solution, prepared by diluting 10 ml of CSF at least 3-fold with PBS, was applied to the gel. The gel was washed with 20 ml PBS containing 2 M NaCl, then 30 ml PBS containing 0.1% TRITON X-100, and finally with 50 ml PBS, and the protein was eluted with 0.1 M sodium citrate (pH 3.0). Using any kind of antibody, L-PGDS can be efficiently adsorbed onto the gel and eluted with 0.1 M sodium citrate (pH 3.0), and the resulting preparation having enzymatic activity was almost homologous in SDS-PAGE. The yield was about 80% and the product was purified as high as 37-fold relative to the original CSF.

Figure 15:
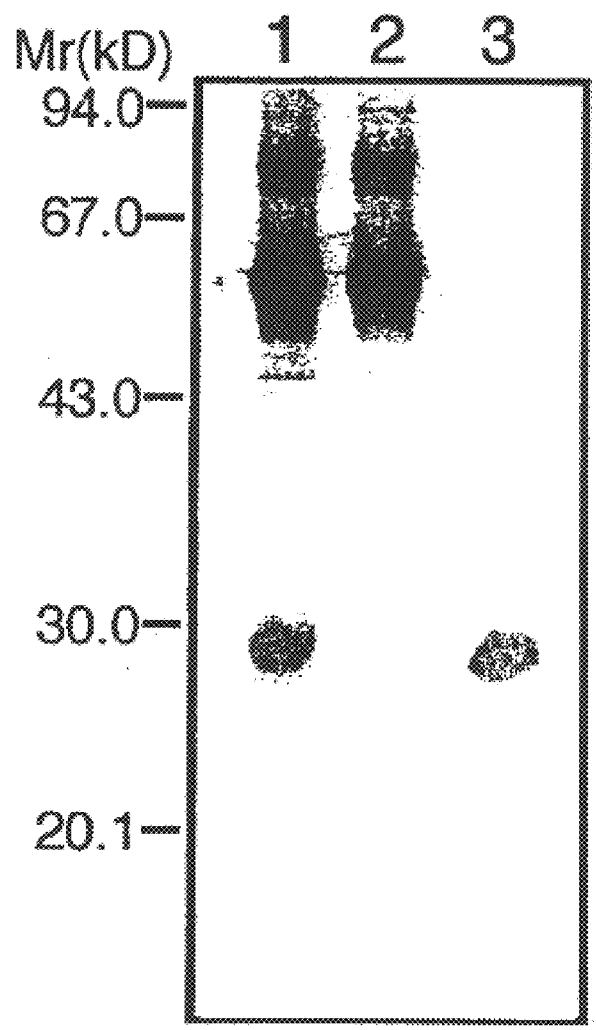
FIG. 15 is a photograph showing a profile in SDS-PAGE of L-PGDS purified by monoclonal antibody.

One Example of such purification is shown in FIG. 15.

Industrial Applicability

According to the present invention, there is provided the monoclonal antibody specific to L-PGDS.

The analysis of the distribution of L-PGDS in the central nervous system is useful for detection of diseases in the central nervous system, and it is expected that L-PGDS levels in CSF or humor can also be used as an indicator in early diagnosis and prognostic observations for other diseases caused by abnormalities in the central nervous system. It is further expected that L-PGDS (β-trace) can be used for examination of a reproduction ability, diagnosis of fetal growth, etc. because this enzyme is distributed in such humors derived from genital organs, as semen, oviduct fluid and amniotic fluid, as well. Further, it was recently revealed in our study that the gene for L-PGDS is expressed in the heart too and therefore the distribution and levels of L-PGDS in blood and other humors can also be used for diagnosis of diseases in the circulatory organs.

Accordingly, the monoclonal antibody provided according to the present invention is useful as a reagent in studying the expression, tissue distribution, physiological action etc. of L-PGDS, and as a reagent for pathological diagnosis of various diseases in the central nervous system as well as in the genital and circulatory organs.

What is claimed is:

1. A monoclonal antibody produced by hybridoma 7F5 or 10A3, deposited as FERM BP-5711 and FERM BP-5713, respectively, wherein the monoclonal antibody specifically recognizes human L-PGDS.

2. A monoclonal antibody produced by hybridoma 9A6, deposited as FERM BP-5712, wherein the monoclonal antibody specifically recognizes human L-PGDS.

3. A monoclonal antibody produced by hybridoma 6F5, deposited as FERM BP-5710, wherein the monoclonal antibody specifically recognizes human L-PGDS.

4. A monoclonal antibody produced by hybridoma 1B7, deposited as FERM BP-5709, wherein the monoclonal antibody specifically recognizes human L-PGDS.

5. A method for detecting L-PGDS comprising contacting L-PGDS with the monoclonal antibody of any of claims 1, 2, 3 or 4.

6. A hybridoma selected from the group consisting of 7F5 or 10A3, deposited as FERM BP-5711 and FERM BP-5713, respectively.

7. The hybridoma 9A6, deposited as FERM BP-5712.

8. The hybridoma 6F5, deposited as FERM BP-5710.

9. The hybridoma 1B7, deposited as FERM BP-5709.

10. A kit comprising one or two monoclonal antibodies that specifically recognize human L-PGDS, wherein the monoclonal antibodies are selected from the group consisting of:

(a) a monoclonal antibody produced by hybridoma 7F5 or 10A3, deposited as FERM BP-5711 and FERM BP-5713, respectively;

(b) a monoclonal antibody produced by hybridoma 9A6, deposited as FERM BP-5712;

(c) a monoclonal antibody produced by hybridoma 6F5, deposited as FERM BP-5710; and (d) a monoclonal antibody produced by hybridoma 1B7, deposited as FERM BP-5709, wherein at least one of the monoclonal antibodies is labeled with an enzyme or is biotinylated.

11. A method of detecting L-PGDS, the method comprising contacting the L-PGDS with one or two monoclonal antibodies that specifically recognize human L-PGDS, wherein the monoclonal antibodies are selected from the group consisting of:

(a) a monoclonal antibody produced by hybridoma 7F5 or 10A3, deposited as FERM BP-5711 and FERM BP-5713, respectively;

(b) a monoclonal antibody produced by hybridoma 9A6, deposited as FERM BP-5712;

(c) a monoclonal antibody specifically recognizing human L-PGDS produced by hybridoma 6F5, deposited as FERM BP-5710; and (d) a monoclonal antibody specifically recognizing human L-PGDS produced by hybridoma 1B7, deposited as FERM BP-5709, wherein at least one of the monoclonal antibodies is labeled with an enzyme or is biotinylated.

* * * * *

```
                              SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
gggaattcat gcacccgagg cc                                            22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gaggtcaggg cgaagccacc                                               20

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ccggatccgc acccgaggcc caggtctcc                                     29

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
atgaattcac tattgttccg tcatgcactt                                    30

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
ccggatcctc cgtgcagccc aacttc                                        26

<210> SEQ ID NO 6
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 6
ccggatccca gccggacaag ttcctg                                              26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ccggatcctc gagctggctc caggag                                              26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ccggatccga tggtggcttc aacctg                                              26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
ccggatccga gacccgaacc atgctg                                              26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
ccggatccta ccggagtccc cactg                                               25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
ccggatccgt ggagactgac tacgacc                                             27

<210> SEQ ID NO 12
<211> LENGTH: 26
<212> TYPE: DNA
<213> ORGANISM: Artificial Sequence
<220> FEATURE:
```

-continued

```
<223> OTHER INFORMATION: Description of Artificial Sequence: Synthetic
      DNA

<400> SEQUENCE: 12
ccggatccgg cgaggacttc cgcatg                                              26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
ccggatccag ggctgagtta aaggag                                              26

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
ccggatccga ggattccatt gtcttcctg                                           29
```